United States Patent [19]
Sandy et al.

[11] Patent Number: 5,427,954
[45] Date of Patent: Jun. 27, 1995

[54] COMPOSITIONS AND METHODS FOR DETECTION AND TREATMENT OF HUMAN OSTEOARTHRITIS

[75] Inventors: John D. Sandy; Carl R. Flannery, both of Tampa; Peter J. Neame, Temple Terrace, all of Fla.; L. Stefan Lohmander, Lund, Sweden

[73] Assignee: Shriner's Hospitals for Crippled Children, Tampa, Fla.

[21] Appl. No.: 875,515

[22] Filed: Apr. 29, 1992

[51] Int. Cl.$^6$ ............................................. G01N 33/00
[52] U.S. Cl. ....................................... 436/89; 436/86
[58] Field of Search ...................... 435/23, 7.71, 7.72, 435/218, 219; 424/85.8; 436/86, 89, 811

[56] References Cited

U.S. PATENT DOCUMENTS 4,810,780  3/1989  Imaizumi et al. .................... 530/350

FOREIGN PATENT DOCUMENTS 0145681  9/1985  European Pat. Off. .

OTHER PUBLICATIONS

Human Tracheal Cartilage Proteoglycan, L92–L107 (1991) Roberts et al.
Virchows Archiv B Cell Pathology; 59(5) (1990) Okada et al. pp. 305–312. (abstract only).
Biochem. J V 274, Feb. (1991) pp. 269–273. Bohm et al.
Lohmander, Stefan (1988) "Proteoglycans of joint cartilage: Structure, function, turnover and role as markers of joint disease" Bailliere's Clinical Rheumatology 2(1):37–62.
Lohmander, L. S., L. Dahlberg, L. Ryd, and D. Heinegard (1990) "Joint Cartilage Markers in Synovial Fluid in Human Osteoarthritis" 36th Annual Meeting, Orthopaedic Research Society, Feb. 5–8, 1990, New Orleans, Louisiana p. 212.
Lohmander, L. Stefan, Leif Dahlberg, Leif Ryd, and Dick Heinegard. Increased Levels of Proteoglycan Fragments in Knee Joint Fluid After Injury. Arthritis and Rheumatism, 32(11):1434–1442; 1989.
Sandy, John D., Carl R. Flannery, Peter J. Neame, and L. Stefan Lohmander. The Structure of Aggrecan Fragments in Human Synovial Fluid. J. Clin. Invest., 89:1512–1516; 1992.
Flannery, Carl R. Michael W. Lark and John D. Sandy. Identification of a Stromelysin Cleavage Site Within the Interglobular Domain of Human Aggrecan. J. of Biol. Chemistry, 267(2):1008–1014; 1992.
Sandy, John D. Peter J. Neame, Raymond E. Boynton, and Carl R. Flannery (1991) "Catabolism of Aggrecan in Cartilage Explants" The Journal of Biological Chemistry 266(14):8683–8685.
Docherty, A. J. P., Gill Murphy (1990) "The tissue metalloproteinase family and the inhibitor TIMP: a study using cDNAs and recombinant proteins" Annals of the Rheumatic Diseases 49:469–479.
Firestein, Gary S., Mary M. Paine, and Bruce H. Littman (1991) "Gene Expression (Collagenase, Tissue Inhibitor of Metalloproteinases, Complement, and HLA-DR) in Rheumatoid Arthritis and Osteoarthritis Synovium" Arthritis and Rheumatism 34(9):1094–1105.
McCachren, S. Spence (1991) "Expression of Metalloproteinases and Metalloproteinase Inhibitor in Human Arthritic Synovium" Arthritis and Rheumatism 34(9):1085–1093.

(List continued on next page.)

*Primary Examiner*—Douglas W. Robinson
*Assistant Examiner*—Anita Varma
*Attorney, Agent, or Firm*—Saliwanchik & Saliwanchik

[57] ABSTRACT

The subject invention concerns novel materials and methods for the detection, treatment, and prevention of human osteoarthritis. Specifically, the cleavage site where aggrecanase cleaves aggrecan has been identified. Identification of this site, as well as the nature of the enzyme, facilitates specific treatments which block or diminish the activity of the enzyme. A further aspect of the invention concerns methods for detecting evidence of osteoarthritis.

3 Claims, No Drawings

OTHER PUBLICATIONS

Murphy, Gilliam, Rosalind M. Hembry, Clare E. Hughes, Amanda J. Fosang, and Tim E. Hardingham (1990) "Role and regulation of metalloproteinases in connective tissue turnover" Biochemical Society Transactions 18:812–815.

Doege, Kurt J., Makoto Sasaki, Tomoatsu Kimura, and Yoshihiko Yamada (1991) "Complete Coding Sequence and Deduced Primary Structure of the Human Cartilage Large Aggregating Proteoglycan, Aggrecan" The Journal of Biological Chemistry 266(2):894–902.

Ratcliffe, Anthongy, Jenny A. Tyler, and Timothy E. Hardingham (1986) "Articular cartilage cultured with interleukin 1: Increased release of link protein, hyaluronate-binding region and other proteoglycan fragments" Biochem. J. 238:571–580.

Lohmander, L. S., and L. Dahlberg (1991) "Proteoglycan Epitope in Join Fluid in Human Osteoarthritis" 37th Annual Meeting, Orthopaedic Research Society, Mar. 4–7, 1991, Anaheim, California, p. 227.

Altman, Roy D., et al. (1987) "Radiographic Assessment of Progression in Osteoarthritis" Arthritis and Rheumatism 30(11):1214–1225.

Lohmander, L. S. (1990) "Osteoarthritis: Man, Models and Molecular Markers" Methods in Cartilage Research 337–340.

Kramer, Jane S., Edward H. Yelin, and Wallace V. Epstein (1983) "Social and Economic Impacts of Four Musculoskeletal Conditions" Arthritis and Rheumatism 26(7)901–907.

COMPOSITIONS AND METHODS FOR DETECTION AND TREATMENT OF HUMAN OSTEOARTHRITIS

BACKGROUND OF THE INVENTION

Joint diseases are a major cause of disability and early retirement in the industrialized countries and are thus of great socioeconomic significance. Of the joint diseases, osteoarthritis (OA) has by far the greatest prevalence, and it has been calculated that, in the United States, OA is responsible for the consumption of up to thirty times more sick-leave days or hospital days than rheumatoid arthritis (Kramer, J. S., E. H. Yelin, W. V. Epstein [1983] *Arthritis Rheum.* 26:901–907). OA is a slowly progressive disease of multifactorial etiology. The rate of disease progress will vary greatly between different patients, depending on the underlying pathogenic factors. Consequently, progress from the very early stages to the overt, clinical stages may take anything from years to decades.

The diagnostic criteria for OA are currently based on the clinical presentation and obligatory radiographic signs (Altman, R. D., J. F. Fries, D. A. Bloch et al. [1987] *Arthritis Rheum.* 30:1214–1225). Since the radiological diagnosis is usually based on a decreased "joint space," it depends on the actual destruction of joint cartilage and will therefore be made only late in the disease. We lack routine methods to diagnose "preOA" or "preradiological" stages of OA, a reflection of our lack of techniques to monitor the joint cartilage in vivo. We are thus unable to determine the ongoing disease activity or the prognosis for the patient threatened by joint cartilage destruction. Moreover, we are unable to monitor with any precision or specificity the effect of pharmacological or surgical intervention aimed at retarding or reversing cartilage destruction in OA or other joint diseases. Any new and improved techniques to diagnose and follow OA need to monitor the present in vivo state of health of the cartilage, not only provide a historical record of past destructive disease.

The details of the mechanisms involved in the disease process of OA are not known. Presumably, the pathogenesis is multifactorial, with genetics, joint malalignment, joint overload or trauma, obesity, and aging as some of the known or suspected contributing factors. Even less well known is how these general factors are translated into disease mechanisms on the tissue and cell level. It may also be that the initiation and progression of OA are controlled by different factors. Since, however, changes in the properties of joint cartilage and loss of matrix components are an integral pan of the disease process, it can be argued that degradation of cartilage matrix is a key event at some time in the development of OA. During this process, matrix molecules, or fragments thereof, are released to the joint fluid and eventually to other body fluids. These molecules and fragments could be used as markers of cartilage turnover in OA and other joint diseases (Lohmander, S. [1988] *Clin. Rheumatol.* 2:37–62; Lohmander, L. S. [1990] "Cartilage markers in joint fluid in human osteoarthritis," In: Brandt, K., ed. *Cartilage changes in osteoarthritis*, Indianapolis: Indiana University School of Medicine Press (ISBN 0-914168-90-8), pp. 98–104; Lohmander, L. S. [1990] "Osteoarthritis: Man, Models, and Molecular Markers," In: Maroudas, A., K. Kuettner, eds. *Methods in Cartilage Research*, London: Academic Press, pp. 337–340).

The aggregating proteoglycan of articular cartilage, or aggrecan, is composed of a protein core to which is attached chondroitin sulfate, keratan sulfate, and both N-linked and O-linked oligosaccharides. The protein core has an extended central segment, to which the glycosaminoglycan chains are attached. At the $NH_2$ terminus, two globular domains, known as G1 and G2, are separated by a short segment known as the interglobular domain (IGD). At the COOH terminus, a single globular domain, G3, is found. The G1 domain is involved in the binding of aggrecan to hyaluronan and link protein, an interaction that probably serves to immobilize the proteoglycan in the tissue (Doege, K., M. Sasaki, T. Kimura, Y. Yamada [1991] *J. Biol. Chem.* 266:894–902).

The catabolism of aggrecan in cartilage explants has been found to involve limited proteolysis of the core protein with the release from the tissue of large chondroitin sulfate-bearing species. Analysis of these major catabolic products with antibodies to the G1 domain and to keratan sulfate (Ratcliffe, A., J. Tyler, T>Hardingham [1986] *Biochem J.* 238:571–580) have indicated that such proteolysis separates the G1 domain from the remainder of the molecule. Interleukin-1α (IL-1α) has been shown to induce increased catabolism of aggrecan in cartilage explants, and high levels of IL-1 in human joint effusions may be responsible for the cartilage degeneration seen in inflammatory joint diseases.

The disease mechanisms active in OA are unclear, but changes in the biochemical and biomechanical properties of joint cartilage, changes in chondrocyte matrix synthesis, and finally, a gradual destruction of the matrix are characteristic of the disease process. Cartilage proteoglycan fragments are released to joint fluid after knee injury and in early stages of both posttraumatic and primary OA in the human (Lohmander, L. S., L. Dahlberg, L. Ryd, D. Heinegard [1989] *Arthritis Rheum.* 32:1434–1442; Lohmander, L. S., L. Dahlberg, L. RYD, D. Heinegard [1990] *Trans. Orthop. Res. Soc.* 15:212 [abstr.]; Lohmander, L. S., L. Dahlberg [1991] *Trans. Orthop. Res. Soc.* 16:227 [abstr.]). An important role for matrix metalloproteinases in both normal turnover of connective tissue matrix and in the tissue destruction seen in, for example, OA has been suggested (Docherty, A. J. P., G. Murphy [1990] *Ann. Rheum. Dis.* 49:469–479; Murphy, G., R. M. Hembry, C. E. Hughes, A. J. Fosang, T. E. Hardingham [1990] *Biochem. Soc. Trans.* 18:812–815), and an imbalance between tissue metalloproteinases and inhibitors has been demonstrated in animal model OA cartilage, in joint fluids from patients with recent joint injury, and in OA joint fluids. Further, increased expression of mRNAs for collagenase, stromelysin, and metalloproteinase inhibitor has been shown in synovial cells stimulated with interleukin-1 and in synovial cells from rheumatoid or osteoarthritic joints (McCachren, S. S. [1991] *Arthritis Rheum.* 34:1076–1084; Firestein, G. S., M. M. Paine, B. H. Littman [1991] *Arthritis Rheum.* 34:1094–1105). However, no definitive evidence has yet been presented which demonstrates that these enzymes are directly involved in cartilage matrix breakdown in OA. A detailed characterization of matrix fragments released from joint cartilage after trauma and in OA of the human could help identify the degradative mechanisms.

Characterization of aggrecan fragments released from bovine explants treated with interleukin-1 in vitro has demonstrated a major cleavage site within the interglobular domain of the proteoglycan core protein which releases large aggrecan fragments from the tissue (Sandy, J. D., P. J. Neame, R. E. Boynton, C. R. Flannery [1991] *J. Biol. Chem.* 266:8683-8685).

BRIEF SUMMARY OF THE INVENTION

The subject invention concerns novel compositions and methods for detection and treatment of aggrecan breakdown associated with human osteoarthritis. Aggrecan is a proteoglycan associated with collagen which constitutes the fibrous protein framework of cartilage. Aggrecanase is an enzyme whose activity is responsible for the pathological breakdown of aggrecan. The subject invention concerns the identification of the cleavage site where aggrecanase cleaves aggrecan. We have further characterized the breakdown products resulting from the proteolytic action of aggrecanase on aggrecan.

From this knowledge of the nature of aggrecanase and its point of action, it is possible to accurately detect the onset of osteoarthritis (OA) or monitor its progression. Also, a further aspect of the invention pertains to the administration of therapeutic agents for the inhibition or prevention of the enzymatic activity of aggrecanase. Thus, in one embodiment of the invention, a metallo or cysteine protease inhibitor is administered to a patient in need of a treatment for osteoarthritis. The protease inhibitor slows or eliminates the enzymatic activity of aggrecanase, thereby alleviating the disease state. A further therapeutic embodiment of the subject invention is the administration, to a person in need of treatment for osteoarthritis, of an effective quantity of proteins or peptides comprising the Glu-Ala cleavage site. These peptides which act as enzyme substrates can reduce the levels of enzyme available for destruction of aggrecan. A further therapeutic embodiment of the subject invention is the administration of antibodies to the specific cleavage site of aggrecan, or the region of the aggrecan molecule comprising the cleavage site. This antibody binds to the aggrecan molecule, preventing aggrecanase from acting at that site. Alternatively, antibodies which bind to the aggrecanase may be administered. These antibodies reduce or eliminate the activity of aggrecanase by binding to the enzyme.

The subject invention further concerns diagnostic methods which comprise the detection of aggrecan breakdown products. These breakdown products can be detected by, for example, assays utilizing antibodies specific for the breakdown products.

DETAILED DESCRIPTION OF THE INVENTION

The subject invention concerns materials and methods for the detection, prevention, and treatment of osteoarthritis (OA). The invention arises from our identification of the cleavage site where aggrecanase acts on human aggrecan. We have also characterized the fragments resulting from the action of aggrecanase on aggrecan.

In the examples which follow, we describe the isolation of aggrecan fragments from joint fluids obtained from patients with recent knee joint injury or early or late stage knee OA. We show that the major aggrecan products present in these synovial fluids are relatively large and are composed of a segment of the interglobular domain attached to the G2 domain, the KS domain, and variable lengths of the chondroitin sulfate domain(s).

Synovial fluid was collected from patients with recent knee injury and from patients with early or late stage OA. Chondroitin sulfate-substituted aggrecan fragments present in these fluids were purified by cesium chloride gradient centrifugation, enzymatically deglycosylated, and fractionated by gel filtration on Superose-12. Each sample contained two major aggrecan core protein populations with apparent molecular masses of about 90 kD and about 150 kD. For all samples, $NH_2$-terminal analysis of both populations gave a single major sequence beginning ARGSV. This $NH_2$ terminus results from cleavage of the human aggrecan core protein at the Glu 373-Ala 374 bond within the interglobular domain between the G1 and G2 domains. We have determined that the release of aggrecan fragments from articular cartilage into the synovial fluid seen at all stages of human OA is promoted by the action of a normal cartilage proteinase (aggrecanase) which cleaves the Glu 373-Ala 374 bond of the interglobular domain.

We have also determined that posttraumatic and OA human synovial fluid contains at least two populations of aggrecan fragments, both of which are relatively large and both of which carry the $NH_2$-terminal sequence ARGSVILXVK, situated within the interglobular domain. It is clear that this $NH_2$ terminus (Ala 374) was not generated by proteolysis during deglycosylation with chondroitinase and keratanase, nor at subsequent stages in the isolation of core proteins; thus, in control studies with deglycosylated calf articular A1D1 aggrecan, the only detectable $NH_2$-terminal sequence obtained, VEVS, corresponded to that expected for the intact molecule. In addition, the $NH_2$-terminal sequence FFGVGGEEDIXVQ (initiating at Phe 342) was obtained after deglycosylation of stromelysin-generated CS-bearing human aggrecan fragments, with no evidence of an NH2-terminal sequence beginning at Ala 374.

Such species would appear to represent the bulk of the CS-bearing fragments present in osteoarthritic human synovial fluid for the following reasons. Firstly, greater than 94% of the fragments recovered from the CsCl gradient were recovered in the D1 fraction. Secondly, all of the fragments in such D1 fractions were present in the void volume on Superose-12 fractionation, and deglycosylation of such samples generated only two populations of aggrecan core protein (termed pools I and II). Thirdly, the only detectable sequence in both pool I and pool II samples was ARGSVILXVK, and the molar yield of this sequence was generally about 25% of the starting protein used in preparation of the samples (assuming a molecular mass of 150 kD for these core proteins). This appears to be a reasonable yield, since two chromatographic steps, with attendant losses, were used in sample preparation for sequencing, and the yield in Edman degradation is often only 40–80% of expected.

The protease responsible for cleavage of the Glu 373-Ala 374 bond in the interglobular domain of aggrecan is widely distributed, and it would appear to be part of a general mechanism for the catabolism of aggrecan in both normal turnover and in pathological situations. This implies that this enzyme is normally expressed by chondrocytes and that overexpression of this activity may be a key event in the pathogenesis of disease states involving accelerated cartilage degradation, such as osteoarthritis.

The finding of this predominant NH$_2$-terminal sequence on aggrecan fragments in all of these situations suggests that the enzyme which cleaves the Glu 373-Ala 374 bond acts on the majority of catabolized molecules and that it catalyzes the most COOH-terminal cleavage within the interglobular domain. It is possible that this enzyme acts secondarily to other proteases which cleave the interglobular domain nearer to the NH$_2$ terminus.

In this regard, it may be relevant that stromelysin-1 cleaves the interglobular domain of human aggrecan (Flannery, C. R., M. W. Lark, J. D. Sandy [1992] *J. Biol. Chem.* 267:1008–1014) at the Asn 341-Phe 342 bond. Further, a proportion of the G1 domain which accumulates in human articular cartilage has Asn 341 as a COOH terminus, indicative of stromelysin-1 action in situ; stromelysin-1 does not, however, appear to catalyze the cleavage of the Glu 373-Ala 374 bond (Flannery et al. [1992], supra).

The protease which cleaves the Glu 373-Ala 374 bond of aggrecan may be a member of the family of matrix metalloproteinases, many of which have now been shown to degrade aggrecan as effectively as stromelysin. Alternatively, it might be a member of the cathepsin group of lysosomal cysteine proteinases (Barrett, A. J., D. J. Buttle, R. W. Mason [1988] *ISI Atlas of Science Biochem.* 256–260). There is direct evidence that in human cartilage in vivo, a proportion of the link protein has been cleaved by cathepsin B, which is presumably derived from the chondrocytes (Nguyen, Q., J. Liu, P. J. Roughley, J. S. Mort [1991] *Biochem. J.* 278:143–147).

The finding that products of this enzyme are present in the synovial fluid of patients 3 days after anterior cruciate ligament rupture, 15 years after medial meniscectomy, and after 10 years of primary OA with extensive cartilage loss, suggests that expression of this activity may be both an early and persistent feature of the chondrocyte response to the joint changes associated with both primary and posttraumatic OA.

Methods

Isolation of aggrecan fragments from joint fluid

Synovial fluid samples were adjusted to 4M guanidine-HCl, 0.05M sodium acetate, 0.1 mM PMSF, 5 mM EDTA, 5 mM iodoacetamide, 1 μg/ml pepstatin, pH 6.8, and centrifuged at 20,000 g for 30 minutes to remove any precipitate. Solid CsCl was then added to a density of 1.45 g/ml and gradients established by centrifugation at 40,000 rpm for 48 hours at 10° C. The tubes were sliced in three equal parts to yield fractions D1 (bottom) to D3, and samples were dialyzed at 4° C. against 0.05M sodium acetate pH 6.8 with protease inhibitors. After a final dialysis against water, the samples were lyophilized, and portions were assayed for total protein or papain digested for assay of glycosaminoglycan. The insoluble gel collected from the top of the gradient tubes was dialyzed and lyophilized together with the top gradient fraction.

Assay and sequencing procedures

Proteoglycan and glycosaminoglycan were determined as chondroitin sulfate (CS) equivalents by dimethylmethylene blue, using shark chondroitin sulfate as standard. Protein was determined using the bicinchoninic acid assay kit from Pierce Chemical Co., Rockford, Ill., with bovine serum albumin as standard.

Amino acid sequence analysis was performed on a sequencer (473A or 477A; Applied Biosystems, Inc., Foster City, Calif.) with on-line phenylthiohydantoin analysis. For deglycosylation, D1 samples in 50 mM Tris acetate, 10 mM EDTA, pH 7.6, were treated at 37° C. with chondroitinase ABC (0.075 U/mg CS) for 2 hours. Samples were adjusted to 5 mM PMSF and 10 mM N-ethylmaleimide and incubated for 1 hour with keratanase (0.1 U/mg starting CS) and finally with keratanase II (0.0025 U/mg starting CS) for a further 1 hour. This procedure resulted in a >90% reduction in the reactivity of all samples with dimethylmethylene blue. Core protein preparations from Superose-12 were concentrated to 0.5 ml and desalted on a fast desalting column eluted with water before drying for sequence analysis.

Following are examples which illustrate procedures, including the best mode, for practicing the invention. These examples should not be construed as limiting. All percentages are by weight and all solvent mixture proportions are by volume unless otherwise noted.

Example 1

Isolation of Aggrecan Fragments from Synovial Fluid

Synovial fluid from seven patients were subjected to CsCl gradient centrifugation and the gradient fractions were assayed for glycosaminoglycan and protein. In all samples, >94% of the glycosaminoglycan and <2.5% of the total protein were recovered from the gradient in the bottom fraction (D1, density≈1.55 g/ml). This indicates that the bulk of the aggrecan fragments present in these synovial fluid samples was of high buoyant density and therefore rich in chondroitin sulfate relative to protein.

A portion of the D1 fragments was analyzed on Sepharose CL-2B in the presence of 5% (wt/wt) hyaluronan and 4% (wt/wt) link protein. The two profiles were very similar and showed the presence of a polydisperse population of CS-bearing fragments (peak Kay≈0.55) which did not form aggregates with hyaluronan and link protein. The fragments eluted later on Sepharose CL-2B than aggrecan monomer from mature human carthage (peak Kav≈0.38), but not as late as a tryptic digest of monomer (peak Kay≈0.70), or a papain digest of monomer (peak Kav≈0.79). The results indicate that aggrecan fragments from these joint fluids completely lack a functional G1 domain and also that they have been cleaved, although not extensively, within the CS-bearing domains.

Consistent with these findings, fractionation of synovial fluid D1 aggrecan fragments on Superose-12 showed that in all cases the CS-bearing species were large enough to be excluded from Superose-12, which has an exclusion limit for dextrans of ≈300 kD. In addition, fractionation of deglycosylated D1 samples on Superose-12 indicated that the major aggrecan core protein species in all samples were in the apparent molecular mass range of 90–150 kD.

Example 2

Characterization of Core Proteins

A detailed analysis of the D1 aggrecan fragments from three patients was carried out. The samples were contaminated to a varying degree with nonaggrecan protein which eluted in the included fractions with an apparent size below 66 kD. This material was presumably "trapped" with the D1 aggrecan during ultracentrifugation, possibly as a result of a high concentration of hyaluronan and protein in these samples. The identity of these proteins was not further investigated.

After deglycosylation, 214 nm absorbance profiles for each sample showed two major peaks (pools I and II). The 214-nm absorbing species were apparently not generated by the deglycosylation step but were present in the starting material.

The proteins eluted in pools I and II were both derived from the high molecular weight CS-bearing aggrecan fragments. Thus, when other portions of D1 samples were purified on Superose-12, and fractions 4–10 were pooled for deglycosylation, the 214-nm profile of these core samples on Superose-12 again showed the characteristic double peak.

Example 3

NH$_2$-Terminal Analysis of Aggrecan Core Proteins from Synovial Fluids

The aggrecan core preparations from Superose-12 chromatography of human synovial fluid samples were taken for NH$_2$-terminal analysis, and the results, with apparent picomole yields, are shown in Table 1.

TABLE 1

NH$_2$-terminal sequence data obtained for D1 aggrecan fragments isolated from synovial fluids and fractionated by Superose-12 gel filtration.

| Synovial fluid | Superose pool | Sequence | Approx yield (pmol) |
|---|---|---|---|
| Patient A | I | ARGSVILXVKP | 33 |
| | II | ARGSV | 32 |
| Patient D | I | AXGXVIL | 10 |
| | II | ARGSVILXVK | 39 |
| Patient F | I | ARGSV | 11 |
| | II | ARGSVILXVKPIFEVXP | 145 |
| Patient G | II | ARGSVIL | 11 |

For all synovial fluids analyzed, and for both pool I and pool II core protein species, the major sequence obtained clearly corresponded to the human aggrecan sequence beginning ARGSVILTVKP, which initiates at Ala 374 within the interglobular domain. Interestingly, the eighth residue could not be detected in any sample, and since this is a threonine in the cDNA-derived sequence, it seems likely that this residue is modified, probably by O-substituted carbohydrate. The finding of the same NH$_2$ terminus on pool I and pool II core species suggests that their separation by size is due to different COOH termini, consistent with limited cleavage within the CS domain(s) as discussed above.

Example 4

Assays for the Detection of Evidence of Osteoarthritis

In one embodiment of the subject invention, aggrecan breakdown products are detected using a monoclonal or polyclonal antibody-based assay. An antibody, or antibodies, to the principal breakdown products described herein can be readily produced utilizing procedures which are well known to those skilled in the art. These antibodies can be used in antibody-based assays and kits such as ELISA systems. For example, biological fluid can be contacted with a solution comprising these antibodies. The biological fluid is, preferably, synovial fluid but for convenience, the biological fluid may also be, for example, urine, serum, or lymph fluid. If breakdown products are present in the biological fluid, then the antibodies will bind to the products. Binding of the antibody to breakdown products can be detected in a number of ways. For example, a second antibody with a detectable label (fluorescent, for example) and which binds to the first antibody can be used to determine if the first antibody bound to any breakdown product.

The assays of the subject invention can be used to detect the onset of osteoarthritis or to monitor the progression of the disease. For example, this assay can be used to evaluate the effectiveness of a treatment for OA.

It should be understood that the examples and embodiments described herein are for illustrative purposes only and that various modifications or changes in light thereof will be suggested to persons skilled in the art and are to be included within the spirit and purview of this application and the scope of the appended claims.

We claim:

1. A method for monitoring changes in cartilage associated with osteoarthritis, and method comprising the detection of aggrecan breakdown products in a sample of biological fluid, from a human suspected or known to have osteoarthritis, wherein said aggrecan breakdown products comprise those pardons of aggrecan that result from a cleavage of aggrecan between amino acids Glu 373 and Ala 374, wherein the presence of said aggrecan breakdown products is detected by (a) obtaining a sample of biological fluid from a human;
   (b) isolating aggrecan fragments from said fluid; and
   (c) analyzing the NH$_2$-terminal sequence of the aggrecan fragments obtained in step (b) to ascertain whether the sequence ARGSV is present;

wherein the presence of the ARGSV sequence indicates the occurrence of osteoarthritis.

2. The method, according to claim 1, wherein said biological fluid is selected from the group consisting of synovial fluid, urine, serum, and lymph fluid.

3. The method, according to claim 1, wherein deglycosylated aggrecan breakdown products have molecular mass of between about 90 kD and about 150 kD, as determined by gel filtration on Superose-12.

* * * * *

UNITED STATES PATENT AND TRADEMARK OFFICE
CERTIFICATE OF CORRECTION

PATENT NO. : 5,427,954
DATED : June 27, 1995
INVENTOR(S) : John D. Sandy, et al

It is certified that error appears in the above-indentified patent and that said Letters Patent is hereby corrected as shown below:

Column 1, line 53: Delete "integral pan of" and insert --integral part of--.

Column 3, line 53: Delete "Detailed Description" and insert --Detailed Disclosure--.

Column 6, line 38: Delete "(peak Kay $\approx$ 0.55)" and insert --(peak Kav $\approx$ 0.55)--.

Column 6, line 42: Delete "carthage" and insert --cartilage--.

Column 6, line 43: Delete "(peak Kay $\approx$ 0.70)" and insert --(peak Kav $\approx$ 0.70)--.

Column 8, line 31: Delete "and method comprising" and insert

--said method comprising--.

Column 8, line 35: Delete "those pardons" and insert --those portions--.

Column 8, lines 51-52: Delete "products have molecular" and insert

--products have a molecular--.

Signed and Sealed this

Nineteenth Day of September, 1995

Attest:

BRUCE LEHMAN

Attesting Officer     Commissioner of Patents and Trademarks